US006982004B1

(12) United States Patent
Malik et al.

(10) Patent No.: US 6,982,004 B1
(45) Date of Patent: Jan. 3, 2006

(54) ELECTROSTATIC LOADING OF DRUGS ON IMPLANTABLE MEDICAL DEVICES

(75) Inventors: Shamim Malik, Temecula, CA (US); Syed F. A. Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 136 days.

(21) Appl. No.: 10/306,648

(22) Filed: Nov. 26, 2002

(51) Int. Cl.
*B05B 5/025* (2006.01)

(52) U.S. Cl. ........................ 118/634; 118/628; 118/309; 118/500

(58) Field of Classification Search ................ 118/620, 118/621, 629, 63, 634, 50, 309, 500, 628; 427/2.24, 2.1, 2.25, 2.28, 476, 457, 486; 361/225–229
See application file for complete search history.

(56) References Cited

U.S. PATENT DOCUMENTS 4,329,383 A 5/1982 Joh ............................. 428/36
4,361,418 A * 11/1982 Tscheppe ..................... 417/54
4,628,859 A * 12/1986 Hines ......................... 118/630
4,684,064 A 8/1987 Kwok ........................ 239/223
4,733,665 A 3/1988 Palmaz ....................... 128/343
4,800,882 A 1/1989 Gianturco ................... 128/343
4,828,840 A 5/1989 Sakamoto et al. .......... 424/474
4,882,168 A 11/1989 Casey et al. ................ 424/468
4,886,062 A 12/1989 Wiktor ....................... 128/343
4,932,353 A 6/1990 Kawata et al. .............. 118/302
4,941,870 A 7/1990 Okada et al. ................. 600/36
4,977,901 A 12/1990 Ofstead ...................... 128/772
5,112,457 A 5/1992 Marchant .................... 204/165
5,165,919 A 11/1992 Sasaki et al. ............... 424/488
5,272,012 A 12/1993 Opolski ................... 428/423.1
5,279,863 A * 1/1994 Escallon ..................... 427/477
5,292,516 A 3/1994 Viegas et al. ............... 424/423
5,298,260 A 3/1994 Viegas et al. ............... 424/486
5,300,295 A 4/1994 Viegas et al. ............... 424/427
5,306,501 A 4/1994 Viegas et al. ............... 424/423
5,328,471 A 7/1994 Slepian ....................... 604/101
5,330,768 A 7/1994 Park et al. .................. 424/501
5,380,299 A 1/1995 Fearnot et al. ............. 604/265
5,399,198 A 3/1995 Ghaisas ...................... 118/629
5,417,981 A 5/1995 Endo et al. ................. 424/486
5,447,724 A 9/1995 Helmus et al. ............. 424/426
5,455,040 A 10/1995 Marchant .................... 424/426
5,462,990 A 10/1995 Hubbell et al. ............ 525/54.1
5,464,650 A 11/1995 Berg et al. .................... 427/2.3
5,569,463 A 10/1996 Helmus et al. ............. 424/426
5,578,073 A 11/1996 Haimovich et al. ............ 623/1
5,605,696 A 2/1997 Eury et al. .................. 424/423
5,609,629 A 3/1997 Fearnot et al. ................. 623/1
5,624,411 A 4/1997 Tuch .......................... 604/265
5,628,730 A 5/1997 Shapland et al. ............. 604/21

(Continued)

FOREIGN PATENT DOCUMENTS

EP 0 301 856 2/1989

(Continued)

OTHER PUBLICATIONS

Anonymous, *Cardiologists Draw—Up The Dream Stent*, Clinica 710:15 (Jun. 17, 1996), http://www.dialogweb.com/cgi/document?reg=106184202959, printed Aug. 25, 2003 (2 pages).

(Continued)

*Primary Examiner*—Chris Fiorilla
*Assistant Examiner*—Yewebdar Tadesse
(74) *Attorney, Agent, or Firm*—Squire, Sanders & Dempsey L.L.P.

(57) ABSTRACT

An apparatus and method for electrostatic loading of drugs on an implantable medical device is disclosed.

34 Claims, 2 Drawing Sheets

18
38
36
22
10
20
34
34
24
32
30

U.S. PATENT DOCUMENTS

| Number | Kind | Date | Inventor | Class |
|---|---|---|---|---|
| 5,641,358 | A * | 6/1997 | Stewart | 118/715 |
| 5,649,977 | A | 7/1997 | Campbell | 623/1 |
| 5,658,995 | A | 8/1997 | Kohn et al. | 525/432 |
| 5,667,767 | A | 9/1997 | Greff et al. | 424/9.411 |
| 5,670,558 | A | 9/1997 | Onishi et al. | 523/112 |
| 5,679,400 | A | 10/1997 | Tuch | 427/2.14 |
| 5,700,286 | A | 12/1997 | Tartaglia et al. | 623/1 |
| 5,702,754 | A | 12/1997 | Zhong | 427/2.12 |
| 5,716,981 | A | 2/1998 | Hunter et al. | 514/449 |
| 5,735,897 | A | 4/1998 | Buirge | 623/12 |
| 5,746,998 | A | 5/1998 | Torchilin et al. | 424/9.4 |
| 5,776,184 | A | 7/1998 | Tuch | 623/1 |
| 5,788,979 | A | 8/1998 | Alt et al. | 424/426 |
| 5,800,392 | A | 9/1998 | Racchini | 604/96 |
| 5,820,917 | A | 10/1998 | Tuch | 427/2.1 |
| 5,824,048 | A | 10/1998 | Tuch | 623/1 |
| 5,824,049 | A | 10/1998 | Ragheb et al. | 623/1 |
| 5,830,178 | A | 11/1998 | Jones et al. | 604/49 |
| 5,837,008 | A | 11/1998 | Berg et al. | 623/1 |
| 5,837,313 | A | 11/1998 | Ding et al. | 427/2.21 |
| 5,851,508 | A | 12/1998 | Greff et al. | 424/9.411 |
| 5,858,746 | A | 1/1999 | Hubbell et al. | 435/177 |
| 5,865,814 | A | 2/1999 | Tuch | 604/265 |
| 5,869,127 | A | 2/1999 | Zhong | 427/2.12 |
| 5,873,904 | A | 2/1999 | Ragheb et al. | 623/1 |
| 5,876,433 | A | 3/1999 | Lunn | 623/1 |
| 5,877,224 | A | 3/1999 | Brocchini et al. | 514/772.2 |
| 5,919,126 | A | 7/1999 | Armini | 600/3 |
| 5,925,720 | A | 7/1999 | Kataoka et al. | 525/523 |
| 5,955,509 | A | 9/1999 | Webber et al. | 514/772.7 |
| 5,971,954 | A | 10/1999 | Conway et al. | 604/96 |
| 5,980,928 | A | 11/1999 | Terry | 424/427 |
| 5,980,972 | A | 11/1999 | Ding | 427/2.24 |
| 5,997,517 | A | 12/1999 | Whitbourne | 604/265 |
| 6,010,530 | A | 1/2000 | Goicoechea | 623/1 |
| 6,010,573 | A | 1/2000 | Bowlin | 118/620 |
| 6,015,541 | A | 1/2000 | Greff et al. | 424/1.25 |
| 6,019,784 | A | 2/2000 | Hines | 623/1 |
| 6,033,582 | A | 3/2000 | Lee et al. | 216/37 |
| 6,042,875 | A | 3/2000 | Ding et al. | 427/2.24 |
| 6,051,576 | A | 4/2000 | Ashton et al. | 514/255 |
| 6,051,648 | A | 4/2000 | Rhee et al. | 525/54.1 |
| 6,056,993 | A | 5/2000 | Leidner et al. | 427/2.25 |
| 6,060,451 | A | 5/2000 | DiMaio et al. | 514/13 |
| 6,060,518 | A | 5/2000 | Kabanov et al. | 514/781 |
| 6,080,488 | A | 6/2000 | Hostettler et al. | 428/423.3 |
| 6,096,070 | A | 8/2000 | Ragheb et al. | 623/1 |
| 6,099,562 | A | 8/2000 | Ding et al. | 623/1.46 |
| 6,110,188 | A | 8/2000 | Narciso, Jr. | 606/153 |
| 6,110,483 | A | 8/2000 | Whitbourne et al. | 424/423 |
| 6,113,629 | A | 9/2000 | Ken | 623/1.1 |
| 6,120,536 | A | 9/2000 | Ding et al. | 623/1.43 |
| 6,120,904 | A | 9/2000 | Hostettler et al. | 428/423.3 |
| 6,121,027 | A | 9/2000 | Clapper et al. | 435/180 |
| 6,129,761 | A | 10/2000 | Hubbell | 623/11 |
| 6,153,252 | A | 11/2000 | Hossainy et al. | 427/2.3 |
| 6,165,212 | A | 12/2000 | Dereume et al. | 623/1.13 |
| 6,174,329 | B1 | 1/2001 | Callol et al. | 623/1.34 |
| 6,203,551 | B1 | 3/2001 | Wu | 606/108 |
| 6,231,600 | B1 | 5/2001 | Zhong | 623/1.42 |
| 6,240,616 | B1 | 6/2001 | Yan | 29/527.2 |
| 6,245,753 | B1 | 6/2001 | Byun et al. | 514/56 |
| 6,251,136 | B1 | 6/2001 | Guruwaiya et al. | 623/1.46 |
| 6,254,632 | B1 | 7/2001 | Wu et al. | 623/1.15 |
| 6,258,121 | B1 | 7/2001 | Yang et al. | 623/1.46 |
| 6,283,947 | B1 | 9/2001 | Mirzaee | 604/264 |
| 6,283,949 | B1 | 9/2001 | Roorda | 604/288.02 |
| 6,284,305 | B1 | 9/2001 | Ding et al. | 427/2.28 |
| 6,287,628 | B1 | 9/2001 | Hossainy et al. | 427/2.3 |
| 6,299,604 | B1 | 10/2001 | Ragheb et al. | 604/265 |
| 6,306,176 | B1 | 10/2001 | Whitbourne | 623/23.59 |
| 6,331,313 | B1 | 12/2001 | Wong et al. | 424/427 |
| 6,335,029 | B1 | 1/2002 | Kamath et al. | 424/423 |
| 6,346,110 | B2 | 2/2002 | Wu | 606/108 |
| 6,358,556 | B1 | 3/2002 | Ding et al. | 427/2.24 |
| 6,379,381 | B1 | 4/2002 | Hossainy et al. | 623/1.42 |
| 6,391,052 | B2 | 5/2002 | Buirge et al. | |
| 6,395,326 | B1 | 5/2002 | Castro et al. | 427/2.24 |
| 6,419,692 | B1 | 7/2002 | Yang et al. | 623/1.15 |
| 6,451,373 | B1 | 9/2002 | Hossainy et al. | 427/2.25 |
| 6,454,193 | B1 | 9/2002 | Busick et al. | 239/690 |
| 6,457,470 | B1 | 10/2002 | Coffee | 128/200.14 |
| 6,494,862 | B1 | 12/2002 | Ray et al. | 604/96.01 |
| 6,503,481 | B1 | 1/2003 | Thurston et al. | 424/45 |
| 6,503,556 | B2 | 1/2003 | Harish et al. | 427/2.24 |
| 6,503,954 | B1 | 1/2003 | Bhat et al. | 514/772.2 |
| 6,506,437 | B1 | 1/2003 | Harish et al. | 427/2.25 |
| 6,527,801 | B1 | 3/2003 | Dutta | 623/1.46 |
| 6,527,863 | B1 | 3/2003 | Pacetti et al. | 118/500 |
| 6,540,776 | B2 | 4/2003 | Sanders Millare et al. | 623/1.15 |
| 6,544,223 | B1 | 4/2003 | Kokish | 604/103.01 |
| 6,544,543 | B1 | 4/2003 | Mandrusov et al. | 424/422 |
| 6,544,582 | B1 | 4/2003 | Yoe | 427/2.24 |
| 6,555,157 | B1 | 4/2003 | Hossainy | 427/2.24 |
| 6,558,733 | B1 | 5/2003 | Hossainy et al. | 427/2.24 |
| 6,565,659 | B1 | 5/2003 | Pacetti et al. | 118/500 |
| 6,572,644 | B1 | 6/2003 | Moein | 623/1.11 |
| 6,585,765 | B1 | 7/2003 | Hossainy et al. | 623/1.45 |
| 6,585,926 | B1 | 7/2003 | Mirzaee | 264/400 |
| 6,605,154 | B1 | 8/2003 | Villareal | 118/500 |
| 6,669,980 | B2 | 12/2003 | Hansen | |
| 6,743,462 | B1 * | 6/2004 | Pacetti | 427/2.24 |
| 6,743,463 | B2 * | 6/2004 | Weber et al. | 427/2.24 |
| 2001/0018469 | A1 | 8/2001 | Chen et al. | 523/121 |
| 2001/0037145 | A1 | 11/2001 | Guruwaiya et al. | 623/1.15 |
| 2002/0077693 | A1 | 6/2002 | Barclay et al. | 623/1.13 |
| 2002/0091433 | A1 | 7/2002 | Ding et al. | 623/1.2 |
| 2002/0133224 | A1 | 9/2002 | Bajgar et al. | 623/1.39 |
| 2002/0155212 | A1 | 10/2002 | Hossainy | 427/2.25 |
| 2003/0054090 | A1 | 3/2003 | Hansen | 427/2.1 |
| 2003/0065355 | A1 | 4/2003 | Weber | 606/200 |
| 2003/0065377 | A1 | 4/2003 | Davila et al. | 623/1.13 |
| 2003/0069634 | A1 | 4/2003 | Bialecke et al. | |
| 2003/0099712 | A1 | 5/2003 | Jayaraman | 424/486 |
| 2003/0185964 | A1 | 10/2003 | Weber et al. | 427/2.25 |

FOREIGN PATENT DOCUMENTS

| | | |
|---|---|---|
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 273 314 | 1/2003 |
| JP | 2001-190687 | 7/2001 |
| WO | WO 91/12846 | 9/1991 |
| WO | WO 95/10989 | 4/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/17331 | 4/1998 |
| WO | WO 98/36784 | 8/1998 |
| WO | WO 99/01118 | 1/1999 |

| | | |
|---|---|---|
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/74414 | 10/2001 |
| WO | WO 01/01890 | 11/2001 |
| WO | WO 02/03890 | 1/2002 |
| WO | WO 02/026162 | 4/2002 |
| WO | WO 02/34311 | 5/2002 |
| WO | WO 02/056790 | 7/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |

OTHER PUBLICATIONS

Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18 (12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ehylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Shigeno, *Prevention of Cerebrovascular Spasm By Bostenan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

* cited by examiner

ELECTROSTATIC LOADING OF DRUGS ON IMPLANTABLE MEDICAL DEVICES

BACKGROUND

This invention relates to an apparatus and method for electrostatic loading of a drug onto an implantable medical device such as a stent.

FIG. 1 illustrates a stent 10 having a conventional design of struts 12 interconnected by connecting elements 14. Struts 12 and connecting elements 14 are separated by gaps 16. Stent 10 is generally cylindrical and radially compressible. Compressible embodiments of stent 10 can be balloon expandable or self-expandable. Although stents work well mechanically, the chronic issues of restenosis and, to a lesser extent, thrombosis remain a significant clinical problem. These events are affected and made worse by the degree of injury and the hemodynamic disturbance caused by the stent. In order to more effectively treat these conditions, pharmacological therapy can be used in conjunction with stent therapy. Maintaining the necessary drug concentration at the lesion site for the necessary period of time remains a challenge, however. This can be done with brute force methods using oral or intravenous administration but the issues of systemic toxicity and side effects arise. Therefore, a preferred route can be achieved by local delivery of drug from the stent itself.

Being made of metal, plain stents are not useful for drug delivery. To serve as a drug reservoir, a coating, usually of a polymer, is applied by dipping or spraying the stent. A solution of a polymer dissolved in a solvent and a therapeutic substance added thereto is applied to the stent and the solvent is allowed to evaporate. A polymeric coating impregnated with a therapeutic substance then remains on the surface of the stent.

This manufacturing process can consume large quantities of solvent and process time. This process can also reduce the capability of batch processing (e.g., processing large stent quantities in single production runs) since each stent is individually sprayed with or dipped into the coating solution. Accordingly, a stent coating process is desired that reduces waste solvent and process time and can facilitate batch processing.

SUMMARY

In accordance with one embodiment of the invention, a method of depositing a therapeutic substance on a stent is provided, comprising ionizing a therapeutic substance; applying an electrical charge to a stent; and exposing the electrically charged stent to the ionized therapeutic substance.

In accordance with another embodiment of the invention, a system for depositing a drug onto a stent is provided, comprising: a chamber for housing a stent; an electrical supply source in communication with the stent for applying an electrical charge to the stent; and a system for ionizing a drug within the chamber so that the drug is attracted to and deposited on the charged stent.

DETAILED DESCRIPTION

Figure 1:
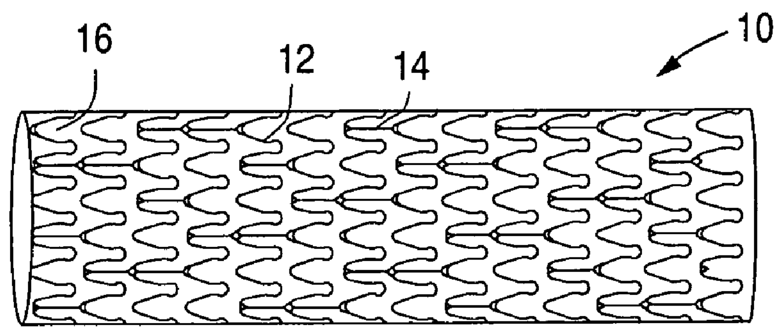
FIG. 1 illustrates a conventional stent.
Figure 2:
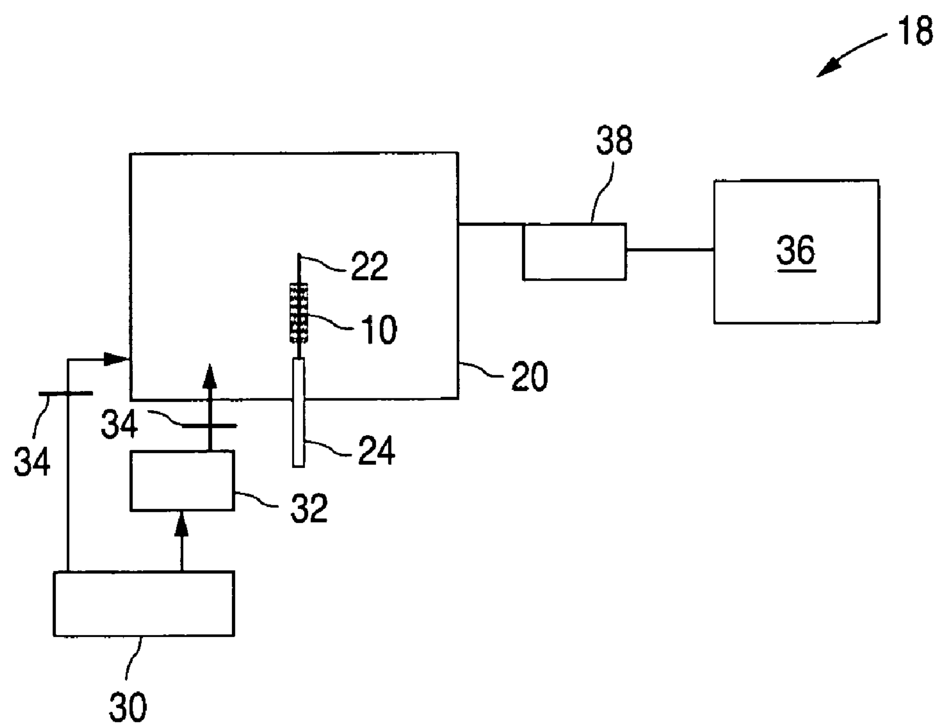
FIG. 2 is a schematic illustration of an embodiment of the coating system.
Figure 3:
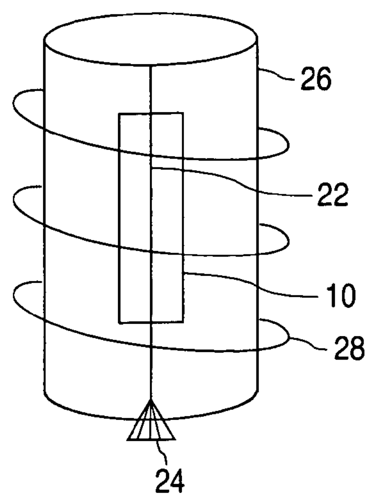
FIG. 3 is one embodiment of the mesh tube in which a stent can be placed surrounded by an RF coil.
Figure 4:
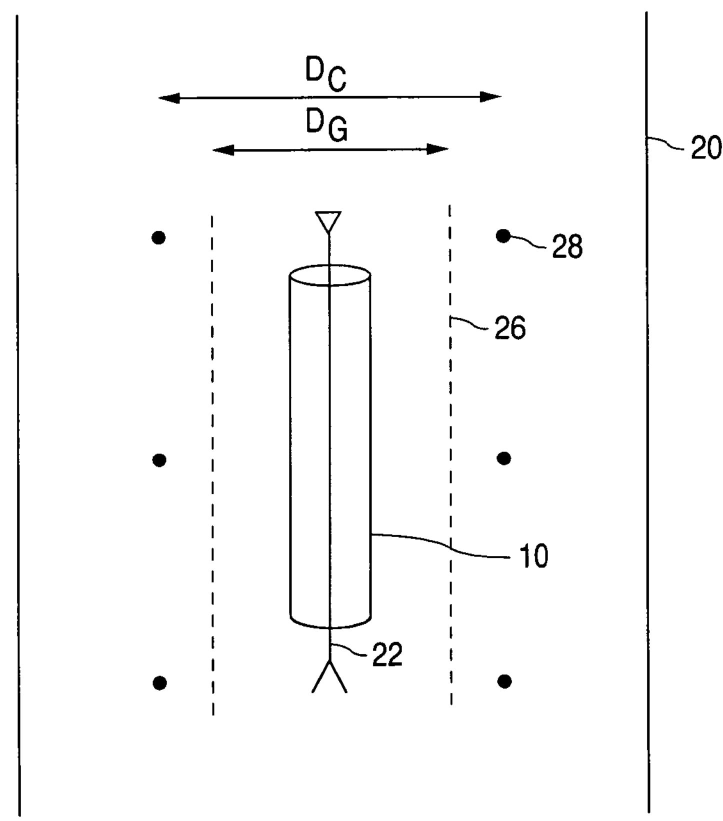
FIG. 4 is one embodiment of the stent, mesh tube, and RF coil inside of a pressure chamber.

FIG. 2 illustrates an embodiment of an agent loading apparatus 18, which includes a chamber 20 housing a stent support apparatus or mandrel 22 for supporting stent 10. Mandrel 22 is placed in electrical contact with an electrical feed 24 within chamber 20. Any suitable chamber 20 can be used, for example chambers that have electrical feed 24 mounted on a KF-40 flange (MDC, Hayward, Calif.). In one embodiment, as illustrated in FIG. 3, a grid or mesh tube 26 can circumscribe mandrel 22 and stent 10. Grid 26 can extract the electrons within the mesh tube and increase the uniformity of the coating surface. Grid 26 can have a tube diameter DG of about 2.5 cm and a thickness of about 0.1 mm. The surface area of the cylinder formed by grid or mesh tube 26 can be about 90% open voids and about 10% mesh. Mesh tube 26 can be connected to a second electrical feed, or can share electrical feed 24 with mandrel 22. An RF coil 28 circumscribes grid 26. The diameter $D_c$ of the coil can be about 5.1 cm.

Referring again to FIG. 2, a gas feed line 30 is in fluid communication with chamber 20 and a loading cavity 32, which in turn is in fluid communication with chamber 20. Loading cavity 32 holds the drugs in powder form. Closeable gates or valves 34 can be used to control the flow of the gas. A pump 36 can also be in fluid communication with chamber 20. Pump 36 can be a turbo pump, a mechanical rough pump, or a cryo pump. A particulate trap 38 can be disposed between pump 36 and chamber 20. One example of trap 38 is a Coaxial 4-line/Roughing Trap (from Varian Inc., Tempe, Ariz.) that attaches to a KF-40 flange. Trap 38 can minimize contamination in the exhaust from reaching pump 36. Trap 38 can filter particles from of up to, for example 10 microns (0.4 mils) in diameter.

One of ordinary skill in the art can understand that a plurality of stents 10 can be loaded onto mandrels 22 placed within chamber 20 in a grid-like or similar configuration to enable batch processing of stents 10. Additionally the medical device need not be limited to stents and a variety of other medical devices which need to be modified to delivery a drug can also be used.

A gas such as argon is introduced into chamber 20 and the pressure is maintained at about 50 to 100 mTorr. A pulsed bias of up to, for example, 50 V is applied to grid 26 while an RF power of, for example, 100 W at a frequency of 13.56 MHz is applied to initiate formation of electrons. Electrons are produced in chamber 20 while grid 26 collects the electrons around stent 10. Loading cavity 32 holds the drug in powder form having particles from about 1 micron (0.04 mils) to about 5 microns (0.2 mils) in diameter. The drug should be electrophilic to facilitate charging of the particles.

A carrier gas can then flow from gas feed line 30 through loading cavity 32, carrying the drug through gate 34 and into chamber 20. The gas should be inert to the biological properties of the drug. For example, gasses of helium, nitrogen, argon, neon, xenon, krypton, or combinations thereof can be used as the carrier. The drug is supplied in bursts, such as in 500 millisecond bursts into chamber 20 which, in effect, can raise the pressure in the chamber up to for example, 500 mTorr. The gas can be introduced at any temperature from about absolute zero to an upper limit temperature of the drug. The upper limit temperature of the drug is defined as the temperature above which the active agent begins to undergo substantial changes that permanently alter its biological efficacy. The upper limit temperature can be determined by one having ordinary skill in the art for each respective drug. Gate 34 can be opened and closed manually, or gate 34 can be closed automatically, for example when the pressure across gate 34 drops below a pre-determined level entered into a gate controller. The pulsed bias applied to grid 26 and RF power are tuned off and a pulsed bias is applied to stent 10 via mandrel 22, for example up to about 50 KV. As a result, the ionized drug is deposited on stent 10.

Stent 10 can be pre-coated with an appropriate coating, for example a carbon pre-coating or deposits or a primer polymer layer, to help adhere the substance to stent 10. The particles can then be compacted onto the surface of stent 10 or on the primer layer. It is believed that this coating method may produce a coating with a thickness from about 0.25 microns (0.0098 mils) to about 3 microns (0.1 mils) with a uniformity with less than about 5% variation in thickness.

Agent loading apparatus 18 and the coating method described herein can be used in conjunction with rotary atomizer or spray chilling apparatuses that coat stent 10 with polymers or polymer and agent combinations. Agent loading apparatus 18 can load an agent onto stent 10 before stent 10 is coated with a polymer or polymer and agent topcoating by a different process. The use of the inventive process and a complementary process can minimize the use of solvents for the agent application processes and enable the coating of large quantities of stents 10 in single batches.

The substance loaded onto the stent can be, for example, any drug capable of inhibiting abnormal or inappropriate migration and/or proliferation of smooth muscle cells for the prevention or inhibition of restenosis. The drug can also be capable of exerting a therapeutic or prophylactic effect such as for example enhancing wound healing in a vascular site or improving the structural and elastic properties of the vascular site.

While particular embodiments of the present invention have been shown and described, it will be obvious to those skilled in the art that changes and modifications can be made without departing from this invention in its broader aspects. Therefore, the appended claims are to encompass within their scope all such changes, modifications, and combinations as fall within the true spirit and scope of the invention.

What is claimed is:

1. A system for depositing a drug onto a stent, comprising:
- a chamber for housing a stent;
- an electrical supply source in communication with the stent for applying an electrical charge to the stent; and
- a system including an RF coil surrounding the stent for ionizing a drug within the chamber so that the drug is attracted to and deposited on the charged stent.

2. The system of claim 1, additionally comprising a pump in fluid communication with the chamber for adjusting the pressure of the chamber.

3. The system of claim 2, additionally comprising a trap positioned between the pump and the chamber for capturing particles of the drug.

4. The system of claim 2, wherein the pump is a turbo pump, a mechanical rough pump or a cryo pump.

5. The system of claim 1, wherein the stent is supported by a support member.

6. The system of claim 5, wherein the support member is in communication with the electrical supply source for applying the electrical charge to the stent.

7. The system of claim 1, additionally comprising a mesh tube disposed between the stent and the RF coil, the mesh tube capable of receiving a charge for collecting charged particles around the stent.

8. The system of claim 7, wherein the mesh tube is in communication with the electrical supply source or is in communication with a second electrical supply source.

9. A system for depositing a drug onto a stent, comprising a drug applicator for directing a drug towards a stent and a system including a coil surrounding the stent for charging the drug so that the drug is attracted to and deposited onto the stent.

10. The system of claim 9, additionally comprising:
- a chamber for housing the stent
- a pump in fluid communication with the chamber for adjusting the pressure of the chamber; and
- a trap positioned between the pump and the chamber for capturing particles of the drug.

11. The system of claim 10, wherein the pump is a turbo pump, a mechanical rough pump or a cryo pump.

12. The system of claim 9, wherein the drug applicator comprises a drug reservoir in communication with a gas source.

13. The system of claim 9, wherein the stent is supported by a support member.

14. The system of claim 13, wherein the support member is in communication with an electrical supply source for applying an electrical charge to the stent.

15. The system of claim 9, additionally comprising an electrical supply source in communication with the stent for applying an electrical charge to the stent.

16. The system of claim 9, additionally comprising a collecting member around the stent, the collecting member capable of receiving a charge for collecting charged particles around the stent.

17. The system of claim 16, wherein the collecting member is located between the stent and the coil.

18. A system for depositing a drug onto an implantable medical device, comprising:
- a support member for supporting a medical device;
- an electrical supply source in communication with the support member for applying an electrical charge to the medical device;
- a system capable of charging a drug so that the drug is attracted to and deposited on the charged medical device; and
- a collecting member circumscribing the medical device, the collecting member capable of receiving a charge for collecting charged particles around the medical device.

19. A system for depositing a drug onto an implantable medical device, comprising:
- a support member for supporting a medical device;
- an electrical supply source in communication with the support member for applying an electrical charge to the medical device; and
- a system capable of charging a drug so that the drug is attracted to and deposited on the charged medical device, wherein the system capable of charging the drug includes a coil surrounding the medical device.

20. A system for depositing a drug onto a stent, comprising:
- a chamber for housing a stent;
- a drug applicator for directing drug particles towards the stent;
- means for charging the drug particles directed towards the stent, the means for charging the drug particles including an RF coil; and a collecting member positioned adjacent to the stent for collecting the charged drug particles around the stent.

21. The system of claim 20, wherein the drug applicator includes a drug source in communication with a gas source.

22. The system of claim 20, additionally comprising means for controlling the pressure in the chamber.

23. The system of claim 20, additionally comprising means for applying a charge to the stent and/or the collecting member.

24. The system of claim 20, wherein the collecting member is positioned between the RF coil and the stent.

25. A system for depositing a drug onto a stent, comprising:

a chamber for housing a stent;

a drug applicator for directing drug particles towards the stent;

means for charging the drug particles directed towards the stent; and a collecting member positioned adjacent to the stent for collecting the charged drug particles around the stent, wherein the collecting member is a mesh body.

26. The system of claim 25, additionally comprising means for applying a charge to the stent and/or the collecting member.

27. A system for depositing a drug onto a stent, comprising:

a chamber for housing a stent;

a drug applicator for directing a drug towards the stent, such that the drug is caused to be charged so that the drug is deposited on the stent;

an RF coil for charging the drug; and a collecting member positioned adjacent to the stent for collecting charged particles around the stent.

28. The system of claim 27, wherein the collecting member is positioned between the RF coil and the stent.

29. The system of claim 27, additionally including means for adjusting the pressure in the chamber.

30. The system of claim 27, wherein the drug applicator includes a drug source and a gas source.

31. The system of claim 27, additionally comprising means for applying a charge to the stent and/or the collecting member.

32. A system for depositing a drug onto a stent, comprising:

a chamber for housing a stent;

a drug applicator for directing a drug towards the stent, such that the drug is caused to be charged so that the drug is deposited on the stent; and a collecting member positioned adjacent to the stent for collecting charged particles around the stent, wherein the collecting member is a mesh tube.

33. The system of claim 32, additionally including means for charging the drug.

34. The system of claim 32, additionally comprising means for applying a charge to the stent and/or the collecting member.

* * * * *